United States Patent [19]

Schut et al.

[11] 4,393,081

[45] * Jul. 12, 1983

[54] METHYL 3-ACETAMIDO-2-(5-METHOXY-INDOL-3-YL) PROPANOATE AND HYPOTENSIVE USE THEREOF

[75] Inventors: Robert N. Schut, Edwardsburg, Mich.; Max E. Safdy, Elkhart, Ind.; Enrique Hong, Cerro San Francisco, Mexico

[73] Assignee: Miles Laboratories, Inc., Elkhart, Ind.

[*] Notice: The portion of the term of this patent subsequent to Aug. 11, 1998, has been disclaimed.

[21] Appl. No.: 315,638

[22] Filed: Oct. 28, 1981

[51] Int. Cl.³ ............... A61K 31/405; C07D 209/20

[52] U.S. Cl. .................... 424/274; 548/496; 548/495

[58] Field of Search ............ 260/326.14 R; 548/496; 424/474

[56] References Cited

U.S. PATENT DOCUMENTS 4,283,410  8/1981  Schut et al. ............... 424/274

*Primary Examiner*—Donald G. Daus
*Assistant Examiner*—D. B. Springer
*Attorney, Agent, or Firm*—Jerome L. Jeffers

[57] ABSTRACT

Disclosed is the novel compound methyl 3-acetamido-2-(5-methoxyindol-3-yl) propanoate which is useful as an anti-hypertensive agent.

2 Claims, No Drawings

METHYL 3-ACETAMIDO-2-(5-METHOXY-INDOL-3-YL) PROPANOATE AND HYPOTENSIVE USE THEREOF

BACKGROUND OF THE INVENTION

We have disclosed in our U.S. Pat. No. 4,283,410 certain tryptophan analogs corresponding to the formula:

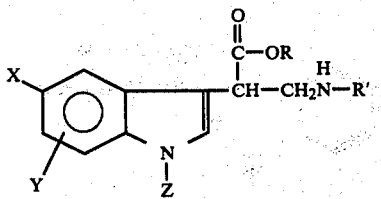

wherein:

R is H, $CH_3$ or $CH_2CH_3$,

R' is H or $\overset{O}{\overset{\|}{C}}CH_3$,

X is H, F or $OCH_3$,

Y is H or Cl, and

Z is H or $\overset{O}{\overset{\|}{C}}OCH_2CH_3$.

Some of the compounds circumscribed by the foregoing formula have potent anti-hypertensive activity, and these compounds are claimed in the '410 patent.

We have now discovered another tryptophan analog which exhibits unexpected potency as an anti-hypertensive agent, which analog is the subject matter of this invention.

SUMMARY OF THE INVENTION

The present invention is methyl 3-acetamido-2-(5-methoxyindol-3-yl) propanoate of the formula:

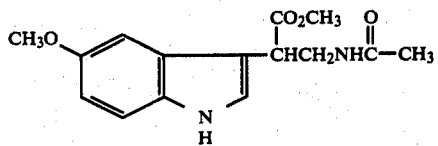

and its use as an anti-hypertensive agent.

DESCRIPTION OF THE INVENTION

The compound of this invention can be prepared by either of two methods using starting materials whose preparation is disclosed in previously mentioned U.S. Pat. No. 4,283,410. The first of these methods is described in following Example I and the second in Example II.

EXAMPLE I

3-Amino-2-(5-methoxy-1H-indol-3-yl) propanoate hydrochloride (10 g) prepared as described in Example 10 of the '410 patent was suspended in $Et_3N$(50 ml) and acetic anhydride (3.6 g; 1 equiv) was added.

The mixture was shaken periodically for 30 minutes and then the solvent removed in vacuo. The residue was treated with $H_2O/CH_2Cl_2$ and the aqueous layer again extracted with $CH_2Cl_2$. The combined $CH_2Cl_2$ was shaken with dilute HCl and then $H_2O$. The $CH_2Cl_2$ was dried over $MgSO_4$ and the solvent removed. Yield, 7.3 g. The viscous liquid was dissolved in refluxing toluene and cooled. The product oiled out but turned solid when stirred with ether. Yield, 6.55 g (m.p. 104°–110°). The solid was dissolved in EtOAc, treated with Nuchar powdered charcoal, filtered, concentrated and ether added. The product oiled out but on scratching the material solidified. The solid was filtered and dried in an Abderhalden apparatus over acetone. Yield, 5.5 g (m.p. 105°–106°) (53.95% yield).

Anal. Calcd. for $C_{15}H_{18}N_2O_4$: C, 62.05; H, 6.25; N, 9.65. Found: C, 61.39; H, 6.13; N, 9.68.

EXAMPLE II 2-(5-Methoxy-1H-indol-3-yl)-3-acetamido propanoic acid (15 g) prepared as described in Example 2 of the '410 patent, was dissolved in 150 ml of MeOH and 6.5 g thionyl chloride added dropwise to a stirred solution in an ice bath. The mixture was stirred overnight at room temperature and the solvent removed in vacuo. The residue was treated with EtOAc/aq. $K_2CO_3$, and the EtOAc extracts combined. The EtOAc was washed with dilute HCl and then $H_2O$. The EtOAc was concentrated to dryness. Yield, 14.5 g. The viscous liquid was dissolved in EtOAc, treated with Nuchar, filtered and concentrated. The solution was treated with ether and some oil came out of solution. The solution was decanted, seeded and allowed to stand at room temperature. The off-white solid was filtered. Yield 9 g (16 g was obtained in another run using 21 g of starting material). The combined solid (25 g) was recrystallized twice from EtOAc/ether. Yield, 19 g (m.p. 105°–106°) (50.2% yield).

Anal. Calcd. for $C_{15}H_{18}N_2O_4$: C, 62.05; H, 6.25; N, 9.65; Found: C, 61.49; H, 6.31; N, 9.33.

EXAMPLE III

Pharmacological Evaluation

This example illustrates the results obtained when the compound of this invention was tested for its ability to lower blood pressure in hypertensive rats.

Rats were made hypertensive by applying a figure-of-eight ligature to one kidney and removing the other kidney two weeks later. At least four weeks elapsed after the second operation, before experimental studies were performed. Indirect systolic blood pressure measurements were made with an occluding cuff and pulse sensor system fitted to the rats' tail. Control blood pressure measurements were made before any compounds were administered. Blood pressure measurements were then made 1,2,4,6, and 8 hours after the oral administration of the test compounds at the dose level of 10 mg/kg. Statistical significance of differences between control and post-treatment values was determined by Wilcoxon's signed rank test (F. Wilcoxon and R. A. Wilcox, Some Rapid Approximate Statistical Procedures, Lederle Laboratories, Pearl River, 1964).

The results of the experimentation described above indicated that changes in blood pressure were −29*, −20*, −23, −17 and −14 mm/Hg at 1,2,4,6 and 8 hours respectively. Asterisks denote that the data are statistically significantly different from the control values. (probability factor less than 0.05).

Administration of the compound of the present invention by conventional means produces a lowering of blood pressure in hypertensive individuals. Medications prepared with this compound as the active ingredient are readily formulated by mixing the compound in dosage units with fillers, carriers, extenders and/or excipients generally used in preparing pharmaceutical formulations. The medication may be either in solid or liquid form and may be compounded as a tablet, powder, capsule, suspension or similar dosage form according to accepted manufacturing methods. The medication can be administered, for example, orally or subcutaneously, in conformity with recognized pharmacological techniques.

What is claimed is:

1. Methyl 3-acetamido-2-(5-methoxyindol-3-yl) propanoate of the formula:

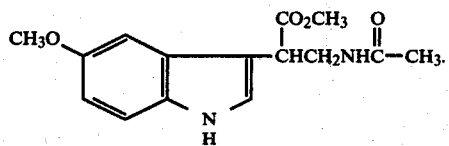

2. A method of treating hypertension in a individual requiring such treatment which comprises administering to such individual an anti-hypertensively effective amount of a compound of the formula:

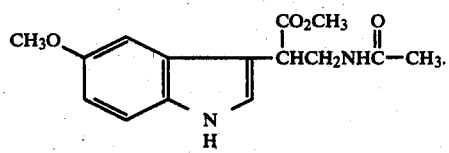

* * * * *